United States Patent [19]

Hartog et al.

[11] 4,125,623

[45] Nov. 14, 1978

[54] SPASMOLYTICS

[75] Inventors: Jan Hartog; Johannes M. A. Zwagemakers, both of Weesp, Netherlands

[73] Assignee: U.S. Philips Corporation, New York, N.Y.

[21] Appl. No.: 724,421

[22] Filed: Sep. 14, 1976

Related U.S. Application Data

[62] Division of Ser. No. 564,777, Apr. 3, 1975, Pat. No. 3,996,245.

[30] Foreign Application Priority Data

Apr. 8, 1974 [NL] Netherlands ............... 7404733

[51] Int. Cl.$^2$ .............................................. A01N 9/28
[52] U.S. Cl. ............................. 424/278; 260/340.9 R; 260/570.5 C

[58] Field of Search ..................... 260/340.9; 424/278

[56] References Cited

U.S. PATENT DOCUMENTS 3,996,245  12/1976  Hartog et al. ............... 260/340.9

*Primary Examiner*—Robert V. Hines
*Attorney, Agent, or Firm*—Frank R. Trifari; Norman N. Spain

[57] ABSTRACT

Tertiary amines of formula 3 have a strong and prolonged spasmolytic effect, also after oral administration, on the smooth musculature of the tractus gastrointestinalis, the tractus urogenitalis and the bronchial system and have a low toxicity.

The compounds can be synthetized according to methods known per se and been formulated to pharmaceutical compositions.

12 Claims, 1 Drawing Figure

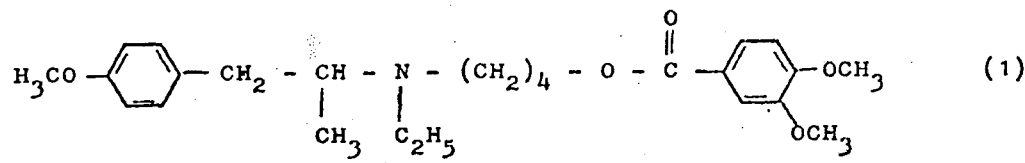 (1)
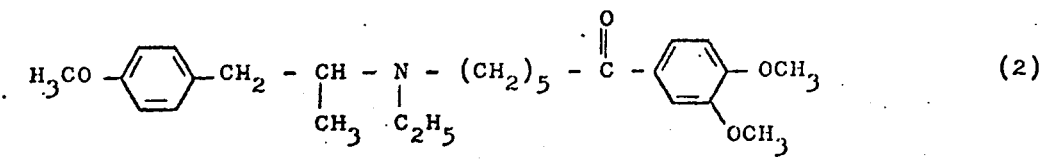 (2)
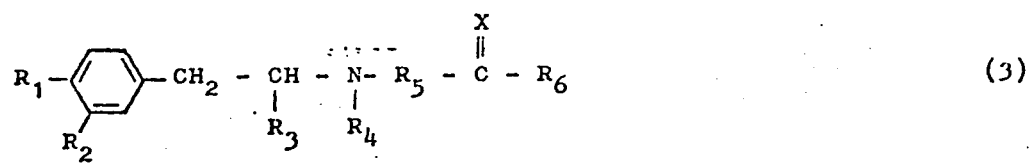 (3)
 (4)
 (5)
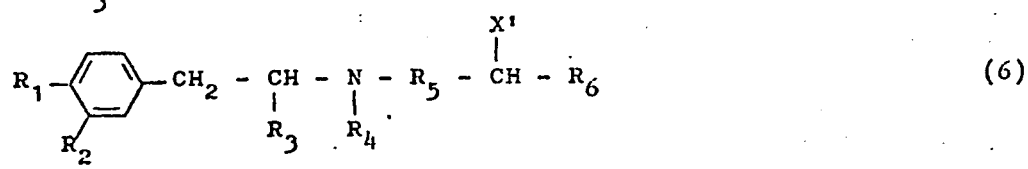 (6)
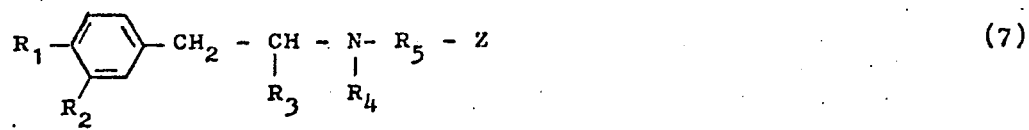 (7)
 (8)
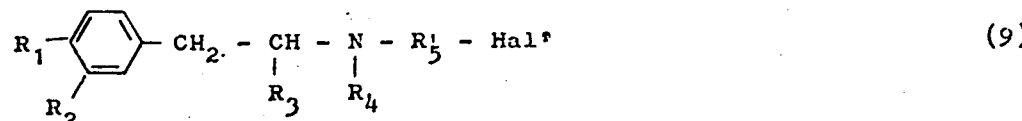 (9)
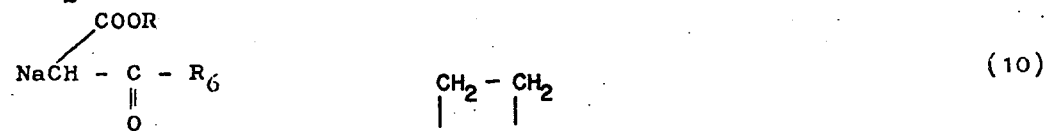 (10)
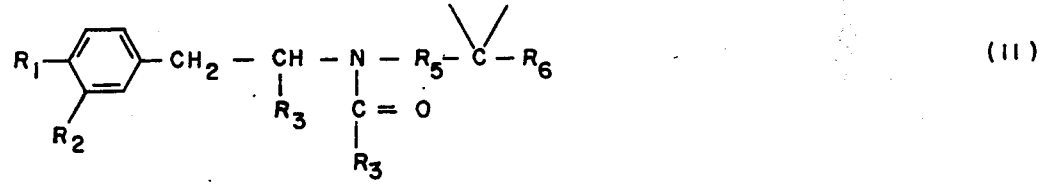 (11)

SPASMOLYTICS

This is a division of application Ser. No. 564,777, filed Apr. 3, 1975, and now U.S. Pat. No. 3,996,245.

The invention relates to spasmolytic compounds, to pharmaceutical compositions and to methods of preparing the compounds and compositions.

The compound of formula 1 is known as a spasmolytic from Dutch Patent Specification No. 112,650, while the compound of formula 2 as a spasmolytic is described in the published Dutch Patent Application No. 6,611,111. Upon oral administration, however, both compounds have only a weak and shortlasting activity.

I is the object of the invention to provide compounds which exert a specific, spasmolytic effect on the smooth musculature of the tractus gastrointestinalis, the tractus urogenitalis and the bronchial system and show said effect also for a long time and to a considerable extent after oral administration.

It has surprisingly been found that compounds of formula 3 and their salts formed with pharmaceutically acceptable acids distinguish considerably from the compounds of formulae 1 and 2 as regards their properties, in spite of the structure relationship.

In formula 3 the symbols have the following meanings: $R_1$ is an alkyl group, an alkoxy group, an alkyl-thio group or a dialkylamino group, which substituents have maximally 2 carbon atoms, a hydroxy group, a hydrogen atom, a chlorine atom, or a fluorine atom; $R_2$ is a hydrogen atom or, if $R_1$ represents a hydrogen atom, moreover one of the remaining substituents summed up for $R_1$, while $R_1$ and $R_2$ both may represent an alkoxy group having 1 or 2 C atoms or together a methylene dioxy or ethylene dioxy group; $R_3$ is an alkyl group having 1 or 2 C atoms; $R_4$ is an alkyl group having 1 to 3 C atoms; $R_5$ is a branched or non-branched alkylene group having 3 to 12 carbon atoms; X is an oxygen atom or an ethylene dioxy group and $R_6$ is a branched or non-branched or cyclised alkyl group having up to 8 C atoms. These compounds are new with the exception of the compound in which $R_1 = OCH_3$, $R_2 = H$, $R_3 = CH_3$, $R_4 = C_2H_5$, $R_5 = (CH_2)_3$, $X = O$ and $R_6 = C_2H_5$, which compound is described in Rec. Trav. Chim., 80 431 (1961) as an intermediate product without the statement of any pharmalogical property whatsoever.

The compounds have a strong spasmolytic activity on the smooth musculature of the tractus gastro-intestinalis, the tractus urogenitalis and the bronchial system. Although said activity has a musculotropic and a neurotropic component, the compounds have no or substantially no peripheral parasympatolytic activities. The compounds exert their activity after parenteral and rectal administration and also after oral administration. Notably the oral effect is considerably stronger and longer lasting than that of the compounds of formulae 1 and 2. This holds good in particular for compounds in which $R_1 = OCH_3$ and $R_2 = H$.

A very strong activity was found in compounds in which $R_5$ has 3 to 5 carbon atoms, in particular in compounds in which $R_6$ is a cyclopentyl group or a cyclohexyl group. The compound in which $R_1 = OCH_3$, $R_2 = H$, $R_3 = CH_3$, $R_4 = C_2H_5$, $R_5 = (CH_2)_3$ $X = O$ and $R_6 = $ cyclo $C_6H_{11}$ and its salts, however, are to be preferred.

On the basis of their properties, the compounds, after having been brought in a form suitable for administration, may be used for the treatment of all kinds of spastic diseases or of hypermotility of the smooth musculature of the tractus gastrointestinalis, the tractus urogenitalis and the bronchial system, for example, for ureteral colic and renal colic, abdominal colics, colitis, postcholocystectomic syndrome, duodenal and ventricular ulcers, spastic colon, "irritable colon" and the like.

The dosis in which the compounds are administered depends on the nature and the severity of the disease to be treated. As a rule, a daily oral dose of from 5 to 50 mg will be chosen for adults. For animals the oral dosage is about 0.1–20 mg per kg.

The compounds have a low toxicity. The $LD_{50}$ values for oral administration are as a rule above 200 mg per kg.

The spasmolytic activity of the compounds of formula 3 was measured inter alia in a test on starved guinea pigs of 500 to 700 gr. The animals were narcotised by intermuscular injection of 1.25 g/kg of urethane. After canules had been inserted into the trache and the vena jugularis, the abdomen was opened and an actively moving loop of the ileum was selected and tied off. The animals were placed at 37° C in a bath containing Tyrode's solution in such manner that the abdomen was fully immersed. The tied-off part of the ileum was connected to a water manometer.

By means of an injection syringe of 20 ml which was connected to the water manometer, the base pressure was adjusted at a value at which no spontaneous contractions occurred. Contractions were produced by the intravenous administration of 2.5 γ carbachol every 7 minutes. The contractions were recorded on a kymograph. After a constant response to the spasmogen had been obtained, a test compound was administered intraduodenally. For that purpose, a thin rubber catheter was inserted orally and secured in the duodenum.

Three minutes after the administration of the test compound, carbachol was injected. The administration of said spasmogen was repeated every 7 minutes.

The contractions as a result of the spasmogen after the administration of the test compound were expressed in percent of the contractions obtained prior to the administration of the test compound. In this manner both the strength and the duration of the activity were determined.

The new compounds of formula 3 and their salts can be obtained by means of methods which are known for the synthesis of this type of compounds and by means of methods analogous thereto.

In agreement herewith, the invention also relates to a method of preparing new tertiary amines, characterized in that compounds of formula 3, in which the symbols have the above-described meanings, and salts thereof formed with pharmaceutically acceptable acids, but with the exception of the compound of formula 3 in which $R_1 = OCH_3$, $R_2 = H$, $R_3 = CH_3$, $R_4 = C_2H_5$, $R_5 = (CH_2)_3$, $X = O$ and $R_6 = C_2H_5$, are prepared according to methods which are known for the preparation of this type of compounds and according to methods analogous thereto.

For example, the compounds can be obtained by reacting a compound of formula 4 with a compound of formula 5. In these formulae $Y_1$ represents either the group

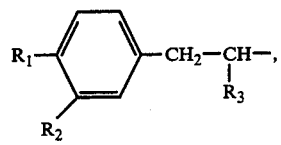

in which case $Y_2$ means the group

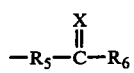

and $Y_3$ the group $R_4$ or conversely, or $Y_1$ represents the group

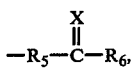

$Y_2$ the group $R_4$ and $Y_3$ the group

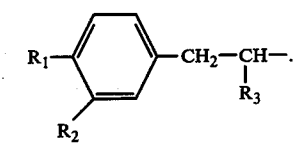

In formula 5, Hal is a halogen atom or a tosyloxy group, but preferably an iodine atom. The reaction is preferably carried out in an inert solvent, for example, acetonitrile, petroleum either, benzene, toluene, acetone, methyl ethyl ketone, methanol and ethanol. The reaction mixture may comprise an acid binder, for example, a tertiary amine such as triethylamine, pyridine and guinoline or an inorganic base, for example, potassium carbonate. An excess of amine of formula 4 may also serve as such. The reaction temperature is between $-20°$ and $200°$ C.

If desired, compounds of formula 3, in which X is an ethylene dioxy group, can be hydrolysed to the corresponding ketones by means of acid. For said hydrolysis, diluted acids may be used, for example, sulphuric acid and hydrochloric acid, possibly mixed with an organic solvent, for example, acetone. The reaction temperature as a rule is between room temperature and the boiling point of the mixture.

Compounds of formula 3 in which X is an oxygen atom may also be obtained by oxidizing a compound of formula 6. Said reaction can be carried out with potassium permanganate or sodium bichromate in, for example, acetone, methyl ethyl ketone, water or acetic acid.

The ketones of formula 3 can also be obtained by reacting a compound of formula 7, in which Z is a nitril group or a lower alkoxycarbonyl group, with a Grignard reagent of formula 8, in which Hal' is a chlorine atom or bromine atom. The reaction may be carried out in ethers, for example, diethyl ether, dioxane, tetrahydrofurane, at temperatures between $-20°$ C and the boiling point of the mixture.

According to another method, the ketones of formula 3 are obtained by reacting a compound of formula 9 with a compound of formula 10, in which Hal' is a chlorine atom or a bromine atom and R is a lower alkyl group, succeeded by saponification and decarboxylation of the formed acid with, for example, dilute acid at temperatures between room temperature and the boiling point of the mixture. $R'_5$ is an alkylene group having 2 to 11 C atoms.

Compounds of formula 3 can furthermore be prepared by reduction of a compound of formula 11 to prepare ketones of formula 3 succeeded by acid hydrolysis of the ketal group. The reduction is carried out with a hydride, for example $LiAlH_4$ in ethers, for example, diethyl ether, dioxane and tetrahydrofurane as a solvent. The reaction temperature as a rule is between $-10$ and the boiling point of the mixture.

As examples of pharmaceutically acceptable acids with which the aminoketones according to the invention can form salts may be mentioned: hydrochloric acid, hydrobromic acid, sulphuric acid, phosphoric acid, p-toluenesulphonic acid, benzoic acid, acetic acid, propionic acid, tartaric acid, succinic acid, citric acid, fumaric acid, maleic acid.

The compounds can be brought in a form suitable for administration by means of methods known per se. The compounds may be mixed with or dissolved in solid or liquid carrier materials. The resulting mixtures or solutions can be processed to pharmaceutical dosage unit forms, for example, capsules, tablets, coated tablets, pills and suppositories.

The invention will be described in greater detail with reference to the ensuing specific examples. If not stated to the contrary in the examples, the compounds were obtained as a high-boiling-point oil, the boiling point of which could not be established as a result of decomposition. Nor was it possible in that case to obtain a crystalising salt. The compounds were characterized by means of NMR—, IR— and elementary analysis.

EXAMPLES (1) 8-[N-ethyl-[1-methyl-2-(4-methoxyphenyl)]ethylamino]octanone-3

A mixture of 9.2 g of N-ethyl-[1-methyl-2-(4-methoxyphenyl)]-ethylamine, 4.85 g of triethylamine, 12 g of 8-bromooctanone-3 and 7 g of sodium iodide and boiled under reflux for 40 hours while stirring in 100 ml of methyl ethyl ketone. After distilling off the solvent, the residue was taken up in 300 ml of water. Extraction was then carried out with $2\times200$ ml of diethyl ether. The ether extract was extracted with $2\times200$ ml of 2N HCl. The acid water phase was them rendered basic with concentrated ammonia, after which the tertiary amine was extracted with $3\times100$ ml of ether. After drying on sodium sulphate the extract was evaporated to dryness, the above-mentioned substance being obtained. Obtained in an analogous manner were:

(2) 9-[N-ethyl[1-methyl-2-(3-methoxyphenyl)]ethylamino]nonanone-6.

(3) 2-[4-[N-ethyl-[1-methyl-2-(4-methoxyphenyl)]ethylamino]butyl]-2-methyl-1,3-dioxolane.

A mixture of 30.9 g of N-ethyl-[1-methyl-2-(4-methoxyphenyl)]-ethylamine, 14.3 g of 2-(4-chlorobutyl)-2-methyl-1,3-dioxolane and 12 g of sodium iodide in 130 ml of methyl ethyl ketone was converted into the title compound in accordance with example 1.

In a manner analogous to Example 3 were contained:

(4) 2-[3-[N-ethyl-[1-methyl-2-(4-methoxyphenyl)]ethylamino]propyl]-2-methyl-1,3-dioxolane.

(5) 2-[5-[N-ethyl-[1-methyl-2-(4-methoxyphenyl)]ethylamino]pentyl]-2-methyl-1,3-dioxolane.
(6) 2-[5-[N-ethyl-[1-methyl-2-(4-methoxyphenyl)]ethylamino]pentyl]-2-ethyl-1,3-dioxolane.
(7) 2-[3-[N-ethyl- [(1-methyl-2-(4-methoxyphenyl)] ethylamino]propyl]-2-t.propyl-1,3-dioxolane.
(8) 2-[3-[N-ethyl-[1-methyl-2-(4-methoxyphenyl)]ethylamino] propyl]-2-propyl-1,3-dioxolane.
(9) 2-[4-[N-ethyl-[1-methyl-2-(4-methoxyphenyl)]ethylamino] butyl]-2-propyl-1,3-dioxolane.
(10) 2-[3-[N-ethyl-[1-methyl-2-(4-methoxyphenyl)]ethylamino] -propyl]-2-butyl-1,3-dioxolane.
(11) 2-[3-[N-ethyl-[1-methyl-2-(4-methoxyphenyl)]ethylamino] -propyl]-2-pentyl-1,3-dioxolane.
(12) 2-[3-[N-ethyl-[1-methyl-2-(4-methoxyphenyl)]ethylamino] -propyl]-2-cyclohexyl-1,3-dioxolane.
(13) 6-[N-ethyl-[1-methyl-2-(4-methoxyphenyl)]-ethylamino] hexanone-2.

12 g of the 1,3-dioxolane obtained according to Example 3 were heated at approximately 90° C for 1 hour in 480 ml of acetone with 42 ml of 2N sulphuric acid. After cooling, the solution was rendered basic with concentrated ammonia (pH 10) and the acetone was evaporated. After the addition of 200 ml of water to the residue, extraction was carried out with 3×100 ml of ether. The ether extract was then extracted with 3×100 ml of 2N HCl, after which the acid water layer was rendered alkaline with concentrated ammonia (pH 10). The free base precipitated as an oil was then taken up in ether (250 ml). After drying on sodium sulphate and evaporating the ether solution to dryness, the title compound was obtained.

The following ketones were obtained in an analogous manner:

(14) 5-[N-ethyl-[1-methyl-2-(4-methoxyphenyl)]-ethylamino] -pentanone-2.
(15) 7-[N-ethyl-[1-methyl-2-(4-methoxyphenyl)]-ethylamino] heptanone-2.
(16) 8-[N-ethyl-[1-methyl-2-(4-methoxyphenyl)]-ethylamino] octanone-3.
(17) 6-[N-ethyl-[1-methyl-2-(4-methoxyphenyl)]-ethylamino] -2-methylhexanone-3.
(18) 7-[N-ethyl-[1-methyl-2-(4-methoxyphenyl)]-ethylamino] -heptanone-4.
(19) 8-[N-ethyl-[1-methyl-2-(4-methoxyphenyl)]-ethylamino] -octanone-5.
(20) 8-[N-ethyl-[1-methyl-2-(4-methoxyphenyl)]-ethylamino] -octanone-5.
(21) 9[N-ethyl-[1-methyl-2-(4-methoxyphenyl)]-ethylamino] -nonanone-6.
(22) 3[N-ethyl-[1-methyl-2-(4-methoxyphenyl)]-ethylamino] -propylcyclohexylketone.
(23) 8-[N-ethyl-[1-methyl-2-phenyl)-ethylamino]-octanone-5]
(24) 3-[N-ethyl-[1-methyl-2-(4-chlorophenyl)]ethylamino] -propylcyclohexylketone. HCl. Melting point 103°-106° C.
(25) 3-[N-ethyl-[1-methyl-2-(4-methoxyphenyl)]-ethylamino] -propylcyclohexylketone.

A solution of 65.6 g cyclohexylbromide in 110 ml of diethylether was converted into the Grignard compound with 9.6 g of magnesium. Added to the Grignard solution with stirring at 20° C within 20 minutes was a solution of 30.7 g of γ-[N-ethyl-[1-methyl-2-(4-methoxyphenyl)] -ethylamino]-butyric acid ethyl ester in 160 ml of dry diethyl ether. The reaction was completed by refluxing for 1 hour, after which the reaction product was decomposed at 0° C with 200 ml of concentrated ammonium chloride solution. After separation of the ether layer, the water layer was extracted with ether (3×200 ml). The resulting ether solution was washed with water (2×100 ml), dried on sodium sulphate and evaporated to dryness. For the removal of a small quantity of starting product, the reaction product was then boiled in a mixture of 800 ml of ethanol, 50 ml of water and 14 g of potassium carbonate for 24 hours. The solvent was then evaporated under reduced pressure and the residue was taken up in 250 ml of ether. The solution was extracted with 3×200 ml of 2N HCl. The aqueous solution was extracted to pH 10 with ether (3×150 ml) after the addition of concentrated ammonia. The product obtained after drying on sodium sulphate and evaporating to dryness was filtered over 500 g of silica gel to remove polar contaminations. The pure ketone was obtained by elution with methylene chloride to which acetone (10 to 25% by volume) had been added. The following ketones were obtained in an analogous manner:

(26) 6-[N-ethyl-[1-methyl-2-(4-methoxyphenyl)]-ethylamino] -n-hexylcyclohexylketone.
(27) 5-[N-ethyl-[1-methyl-2-(4-methoxyphenyl)]-ethylamino] -pentanone-2.
(28) 5-[N-ethyl[1-methyl-2-(4-methoxyphenyl)]-ethylamino] -3-methylpentanone-2.
(29) 3-[N-ethyl-[1-methyl-2-(4-methoxyphenyl)]-ethylamino] -propylcyclohexylketone hydrochloride.

1.75 ml of 3.4 N ethanolic hydrochloric acid were added to 2.1 g of the base obtained according to Example 25 in 25 ml of ether, after which the solvents were evaporated under reduced pressure. The resulting resinous substance was crystallized from 15 ml of isopropyl ether. Melting point 92°-95° C. In a manner analogous to Examples 25 and 29 was obtained:

(30) 9-[N-ethyl-[1-methyl-2-(4-methoxyphenyl)]-ethylamino] -n-nonylcyclohexylketone hydrochloride. Melting point 69°-72° C.
(31) 5-[N-ethyl-[1-methyl-2-(4-methoxyphenyl)]-ethylamino] -pentanone-2.

The title compound was obtained in the manner described in Example 25 starting from 5.2 g of γ-[N-ethyl[1-methyl-2-(4-methoxyphenyl)]-ethylamino]-butyronitrile in 30 ml of ether and a Grignard compound prepared from 4.25 g of methyl iodide and 0.72 g of magnesium in 25 ml of ether.
(32) 3-[N-ethyl-[1-methyl-2-(4-methoxyphenyl)]-ethylamino] -propylcyclohexylketone A solution of 7.7 g of cyclohexoyl acetic acid ethyl ester in 40 ml of dry benzene was added to a suspension of 0.68 g of sodium powder in 15 ml of toluene. The mixture was stirred at 50° C for 30 minutes, after which a solution of 7.6 g of 2-[N-ethyl-[1-methyl-2-(4-methoxy-phenyl)]-ethylamino]-ethylchloride in 7.5 ml of dry benzene was added dropwise with stirring in 10 minutes. After stirring for 5 hours at 55° C, the whole was cooled to room temperature after which it was washed with water (2×100 ml). The residue obtained after drying on sodium sulphate and evaporation to dryness was heated on a steam bath for 16 hours with 40 ml of 2N sulphuric acid. After cooling, the mixture was rendered basic by the addition of potassium carbonate (11.35 g). After the addition of another 100 ml of water, it was extracted with ether (3×100 ml). After drying on sodium sulphate, the extract was evaporated to dryness and the residue was chromatographed over 270 g of silica gel in methylene chloride to which 10% by volume of acetone had been added. In this manner the title compound was obtained. According to a NMR analysis, the substance was identical to the product obtained according to example 25. In a manner analogous to Example 32 was obtained:

(33) 7-[N-ethyl[1-methyl-2-(4-methoxyphenyl)]-ethylamino] -heptanone-4.

As examples of pharmaceutical compositions may be mentioned:
(34) Capsules containing
   25 mg of active substance
   25 mg of lactose
   0.5 mg of polyvinylpyrrolidon
   4.0 mg of carboxymethylcellulose
   1.0 mg of magnesium stearate.
(35) Tablets of the composition stated in Example 36.
(36) Suppositories containing
   10 mg of active substance
   1490 mg of oleum cocoa
(37) Injection liquid containing
   10 mg of active substance
   15 mg of benzyl alcohol
   pyrogen-free distilled water to 1 ml.

What is claimed is:

1. A spasmolytic composition comprising a spasmolytically effective amount of a compound of the formula

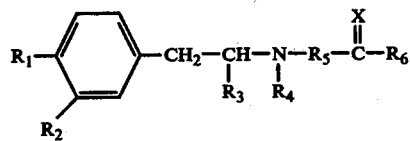

in which $R_1$ represents an alkyl group, an alkoxy group, an alkylthio group or a dialkylamino group having up to 2 carbon atoms per substituent, a hydroxy group, a hydrogen atom, a chlorine atom or a fluorine atom, $R_2$ is a hydrogen atom or, if $R_1$ represents a hydrogen atom, in addition one of the remaining meanings of $R_1$, while $R_1$ and $R_2$ both may represent an alkoxy group having up to 2 carbon atoms, $R_3$ is an alkyl group having up to 2 carbon atoms, $R_4$ is an alkyl group having up to 3 carbon atoms, $R_5$ is a branched or non-branched alkylene group having 3 to 12 carbon atoms, X is an ethylene dioxy group, $R_6$ is a branched or non-branched or cyclised alkyl group having up to 8 carbon atoms and $R_5$ together with $R_6$ contains at least 6 carbon atoms and salts thereof formed with pharmaceutically acceptable acids and a pharmaceutically acceptable carrier therefor.

2. The spasmolytic composition of claim 1 wherein the compound is 2-[3-[N-ethyl-[1-methyl-2-(4-methoxyphenyl)]ethylamino]-propyl]-2-methyl-1,3-dioxolane.

3. The spasmolytic composition of claim 1 wherein the compound is 2-[4-[N-ethyl-[1-methyl-2-(4-methoxyphenyl)]-ethylamino]-butyl]-2-methyl-1,3-dioxolane.

4. The spasmolytic composition of claim 1 wherein the compound is 2-[5-[N-ethyl-[1-methyl-2-(4-methoxyphenyl)]-ethlyamino]-pentyl]-2-methyl-1,3-dioxolane.

5. The spasmolytic composition of claim 1 wherein the compound is 2-[5-[N-ethyl-[1-methyl-2-(4-methoxyphenyl)]-ethylamino]-pentyl]-2-ethyl-1,3-dioxolane.

6. The spasmolytic composition of claim 1 wherein the compound is 2-[3-[N-ethyl-[1-methyl-2-(4-methoxyphenyl)]-ethylamino]-propyl]-2-i.propyl-1,3-dioxolane.

7. The spasmolytic composition of claim 1 wherein the compound is 2-[3-[N-ethyl-[1-methyl-2-(4-methoxyphenyl)]-ethylamino]-propyl]-2-propyl-1,3-dioxolane.

8. The spasmolytic composition of claim 1 wherein the compound is 2-[4-[N-ethyl-[1-methyl-2-(4-methoxyphenyl)]-ethylamino]-butyl]-2-propyl-1,3-dioxolane.

9. The spasmolytic composition of claim 1 wherein the compound is 2-[3-[N-ethyl-[1-methyl-2-(4-methoxyphenyl)]-ethylamino]-propyl]-2-butyl-1,3-dioxolane.

10. The spasmolytic composition of claim 1 wherein the compound is 2-[3-[N-ethyl[1-methyl-2-(4-methoxyphenyl)]-ethylamino]-propyl]-2-pentyl-1,3-dioxolane.

11. The spasmolytic composition of claim 1 wherein the compound is 2-[3-[N-ethyl-[1-methyl-2-(4-methoxyphenyl)]-ethylamino]-propyl]-2-cyclohexyl-1,3-dioxolane.

12. A method of treating a patient suffering from a spastic condition comprising administering to said patient the spasmolytic composition of claim 1 in a spasmolytically effective amount.

* * * * *